United States Patent [19]

Giddings

[11] Patent Number: 5,193,688
[45] Date of Patent: Mar. 16, 1993

[54] METHOD AND APPARATUS FOR HYDRODYNAMIC RELAXATION AND SAMPLE CONCENTRATION NIN FIELD-FLOW FRACTION USING PERMEABLE WALL ELEMENTS

[75] Inventor: John C. Giddings, Salt Lake City, Utah

[73] Assignee: University of Utah, Salt Lake City, Utah

[21] Appl. No.: 726,370

[22] Filed: Jul. 5, 1991

Related U.S. Application Data

[63] Continuation-in-part of Ser. No. 447,630, Dec. 8, 1989, abandoned.

[51] Int. Cl.⁵ .................................... B03B 5/00
[52] U.S. Cl. ........................... 209/155; 209/127.1; 209/210; 209/422; 210/748
[58] Field of Search ............... 209/1, 155, 208–210, 209/156, 39, 40, 127.1, 129, 130, 422, 12, 454, 11; 210/478, 495, 511, 222; 73/865.5

[56] References Cited

U.S. PATENT DOCUMENTS

| | | | |
|---|---|---|---|
| 4,147,621 | 4/1979 | Giddings | 209/155 X |
| 4,214,981 | 7/1980 | Giddings | 209/155 |
| 4,737,268 | 4/1988 | Giddings | 209/210 X |
| 4,894,146 | 1/1990 | Giddings | 209/210 X |
| 4,894,172 | 1/1990 | Williams | 209/155 X |
| 5,039,426 | 8/1991 | Giddings | 209/210 |

Primary Examiner—Donald T. Hajec

[57] ABSTRACT

A new field flow fractionation process for the separation of particles using a modified channel structure to achieve hydrodynamic relaxation without involving a stop-flow procedure and thus provide improved speed of operation as well as improved sample concentration, the new improved channel structure comprising a thin channel having one or more permeable wall sections contained in the enclosing wall or walls of the channel, the permeable wall sections making up not more than 25% of the total wall area of the channel, and adjustable flow control valves for controlling the flowrate of any fluid at the inlet end of the channel and independent flow control valves for controlling the flow rate of the fluid being introduced into or withdrawn from the permeable wall sections.

27 Claims, 7 Drawing Sheets

METHOD AND APPARATUS FOR HYDRODYNAMIC RELAXATION AND SAMPLE CONCENTRATION NIN FIELD-FLOW FRACTION USING PERMEABLE WALL ELEMENTS

Work on this invention was supported by funding from the National I.H. Contract GM 10851-33.

This application is a continuation-in-part of my application Ser. No. 447,630 filed Dec. 8, 1989, now abandoned.

BACKGROUND OF THE INVENTION

1. Field of the Invention

This invention relates to an improved process for the fractionation of particles and an apparatus for conducting the same. More particularly, the invention relates to a field-flow fractionation process utilizing a new type of channel construction which permits one to achieve hydrodynamic relaxation and improved sample concentration.

Specifically, the invention provides a new field-flow fractionation process for the separation of samples of particles and macromolecules which uses a modified channel structure to achieve hydrodynamic relaxation without involving a stop-flow procedure and thus provides improved speed of operation as well as improved sample concentration. The new process of the invention comprises an improvement in the field-flow fractionation (FFF) process wherein a sample carrier fluid containing the particles to be separated is forced through a thin flow channel having one or more inlets and one or more outlets and a field or gradient is used to induce a driving force acting across the thin dimension of the channel perpendicular to the flow axis, the improvement of which comprises employing one or more permeable wall sections in the enclosing wall or walls of the channel and forcing substreams of fluid to enter or exit through the permeable wall sections, the said permeable wall sections making up not more than 25% of the total wall area of the channel.

The invention further provides an apparatus for conducting the above-described process comprising an elongated flow channel enclosed by wall elements, means for applying a driving force perpendicular to the long axis of the channel, one or more inlet means for introducing fluid into one end of the enclosed channel, one or more outlet means for withdrawing fluid from the other end of the channel, the enclosing wall elements including one or more permeable wall sections that are so constructed that substreams of fluid can be forced into or withdrawn from the channel through the permeable wall sections, said permeable wall sections making up less than 25% of the total wall area enclosing the channel, and adjustable flow control means for controlling the flowrate of the fluid at the inlet means and independent control means for controlling the flowrate of the fluid being introduced into or withdrawn from the permeable wall sections.

2. Prior Art

There is a growing need in industry and health sciences for the separation and characterization of micron sized particles including biological cells, latices, environmental particles, industrial powders, crystallization products, and related particulate matter. There is also a growing need for the separation of submicron sized particles, macromolecules and synthetic polymers.

Various methods have been proposed, but in general, they have been too slow, complex in operation, inefficient and expensive or have failed to effect the separation with the desired degree of resolution needed for commercial operations.

Some of the highest resolutions techniques disclosed have been those based on field-flow fractionation as disclosed in the following U.S. patents and copending patent applications: U.S. Pat. Nos. 3,449,938, 4,147,621, 4,214,981, 4,250,026, and copending patent application—Giddings—"Lift-Induced Hyperlayer Field-Flow Fractionation Process for Particle Separation" Ser. No. 153,774, filed Feb. 8, 1988, U.S. patent application—Giddings—"High Speed Separation of Ultra-High Molecular Weight Polymers by Hyperlayer Field-Flow Fractionation" Ser. No. 217,707, filed Jul. 11, 1988, and U.S. patent application—Williams—"Process for Programming of Field-Flow Fractionation" Ser. No. 237,188, filed Aug. 29, 1988.

Other methods for particle separation are disclosed in U.S. Pat. No. 4,737,268 and copending patent application Giddings—"Process for Continuous Particle and Polymer Separation in Split-Flow Thin Cells using Flow-Dependent Lift Forces" Ser. No. 194,851, filed May 17, 1988.

Many articles, such as Giddings et al—"Fast Particle Separation by Flow/Steric Field-Flow Fractionation"—Anal. Chem. (1987) 59 1957, have been published disclosing modifications in the particle separation processes.

While the FFF process and modifications as noted above have met with considerable commercial success, the use has been limited for certain operations because of limitations as to speed of operation and loss of sample material due to adhesion to the wall. The basis for such limitations is noted below.

In virtually any kind of field-flow fractionation process, a relaxation step must be carried out in the FFF channel prior to the beginning of effective separation. In the relaxation process, sample material that is distributed widely over the stream lines entering the channel is forced into narrow cross-sectional distributions from which separation is possible. Normally sample is driven close to one wall (the accumulation wall) of the channel during relaxation by the same external field or gradient that is used to implement FFF separation. In most cases the axial flow is halted as relaxation takes place in order to control band distortion and broadening. This so-called stopflow procedure often leads to flow instabilities accompanied by baseline shifts and provides a window of vulnerability in which particles are most susceptible to adhesion to the channel wall. It also increases run time.

Various methods have been proposed to avoid the stopflow procedure. One of the methods 1 have proposed makes use of hydrodynamic relaxation, a process in which the sample is driven close to its equilibrium position by the manipulation of flow rather than by sluggish field-driven transport in the channel. In this method, hydrodynamic relaxation is carried out by using a flow splitter at the inlet end of the FFF channel. Manipulation of the flow rates of the incoming flow streams entering above and below the splitter make it possible to drive the sample, contained exclusively in the substream emerging from below the splitter, close to the accumulation wall of the channel, a position from which separation can quickly commence.

A second flow splitter can be used at the outlet of the channel to concentrate the component materials for enhanced detection. It has been shown that an outlet flow splitter is capable of stripping off the bulk of liquid flowing above the sample layers in the channel, thus leaving the sample in a more concentrated form for detection and collection.

There are, however, several disadvantages with the use of flow splitters in FFF systems for the above purposes. First, for proper operation these splitters must be suspended evenly across the several centimeter wide gap of the thin channel; unevenness amounting to a few tens of micrometers would noticeably distort the hydrodynamic relaxation process. A second difficulty is that the introduction of a flow splitter and the two associated flow spaces on either side of the splitter, three layers in all, is very often inconsistent with the utilization of very thin, say 100–200 μm, high performance FFF channels. Third, since the flow stream in which sample is introduced must traverse the narrow gap on one side of the splitter where the thickness is only a fraction, ususally approximately one third, of that of the full channel, there is an enhanced risk that larger particles in the sample, whether part of the sample or part of an impurity will clog all or part of the streampath needed for sample introduction. Fourth, at high flowrates the abrupt change in flow direction at the splinter edges may introduce eddy currents in the fluid capable of disrupting the distribution of components near the inlet and outlet.

It would therefore be highly advantageous to find a promising method for the modification of the FFF process to achieve hydrodynamic relaxation and sample concentration wihout any of the above-noted disadvantages.

It is an object of the invention, therefore, to provide an improved FFF process which achieves hydrodynamic relaxation without any of the forementioned problems. It is a further object to provide a new FFF process which effects a reduction in the relaxation effect and eliminates the stop-flow procedure. It is a further object to provide a modified FFF process which is capable of effecting separation as a high rate of speed. It is a further object to provide a modified FFF process which gives hydrodynamic relaxation and improved sample concentration. It a further object to provide an improved FFF process which can be adapted to any of the above-noted FFF techniques. These and other objects of the invention will be apparent from the following detailed description thereof.

SUMMARY OF THE INVENTION

It has now been discovered that these and other objects can be accomplished by the new process of the invention which presents for the first time an efficient technique for reducing adverse relaxation effects without the stop-flow procedure and giving improved sample concenetration in the FFF process.

The new process of the present invention comprises an improvement in the FFF technique wherein a carrier fluid containing the particles to be separated is forced through a thin flow channel having one or more inlets and one or more outlets and a field or gradient is used to induce a driving force acting across the thin dimension of the channel perpendicular to the flow axis, the improvement of which comprises employing one or more permeable wall sections in the wall elements enclosing the channel and forcing substreams of fluid to enter or exit through the permeable wall sections, the said permeable wall sections making up not more than 25% of the total wall area enclosing the channel.

The apparatus for use in effecting the above-noted new process comprises an elongated flow channel enclosed by wall elements, means for applying a driving force perpendicular to the long axis of the channel, one or more inlet means for introducing fluid into one end of the enclosed channel, one or more outlet means for withdrawing fluid from the other end of the channel, a portion of the enclosing wall consisting of one or more permeable wall sections that are so constructed that substreams of fluid can be forced into or withdrawn from the channel through the permeable wall sections, said permeable wall sections making up less than 25% of the enclosing wall area of the channel, and adjustable flow control means for controlling the flow rate of the fluid at the inlet means and independent control means for controlling the flowrate of the fluid being introduced into or withdrawn from the permeable wall sections.

It has been surprisingly found that by the use of the new technique of employing permeable wall sections as described above one can achieve hydrodynamic relaxation without need of a stopflow procedure and thus effect an increase in the speed of operation. In addition, it has been found that the new technique effects a great improvement in sample concentration.

The new process is applicable to virtually all forms of FFF including sedimentation FFF, thermal FFF, electrical FFF and flow FFF in both steric and normal modes of operation. It is particularly effective for flow FFF for which much of the wall area is generally permeable (made up of permeable frit material) to begin with. All that is needed is to isolate by a sealing arrangement one or more small feed chambers above the areas selected to be permeable wall sections as described hereinafter.

DESCRIPTION OF THE DRAWINGS

The various objects and features of the present invention can be more fully understood by reference to the accompanying drawings.

Figure 1:
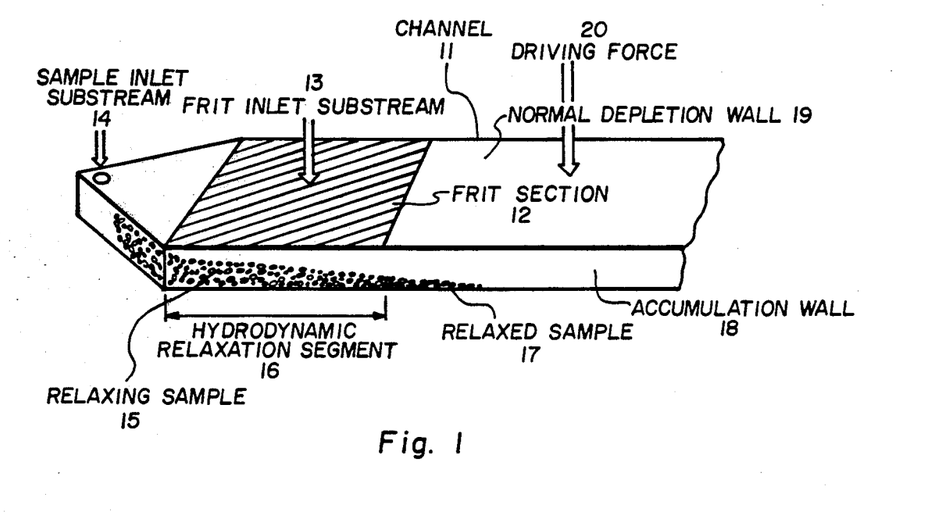
FIG. 1 is a diagram showing one possible configuration of a permeable wall (frit) element or section incorporated in the depletion wall at the inlet end of an FFF channel. By permeating the frit inlet substream through the frit section, the sample-containing substream is driven toward the accumulation wall, thus bringing about hydrodynamic relaxation.

With reference to FIG. 1 which illustrates the presence of frit section 12 at the inlet end of the FFF channel 11, the carrier flow entering through the frit section by means of the frit inlet substreams is shown as 13, the sample inlet substream as 14, the sample being relaxed as 15 through segment 16 and relaxed sample as it enters the rest of the channel as 17. The accumulation wall near which the sample is driven is shown as 18, the depletion wall on the opposite side of the channel as 19 and the driving force as 20.

Figure 2:
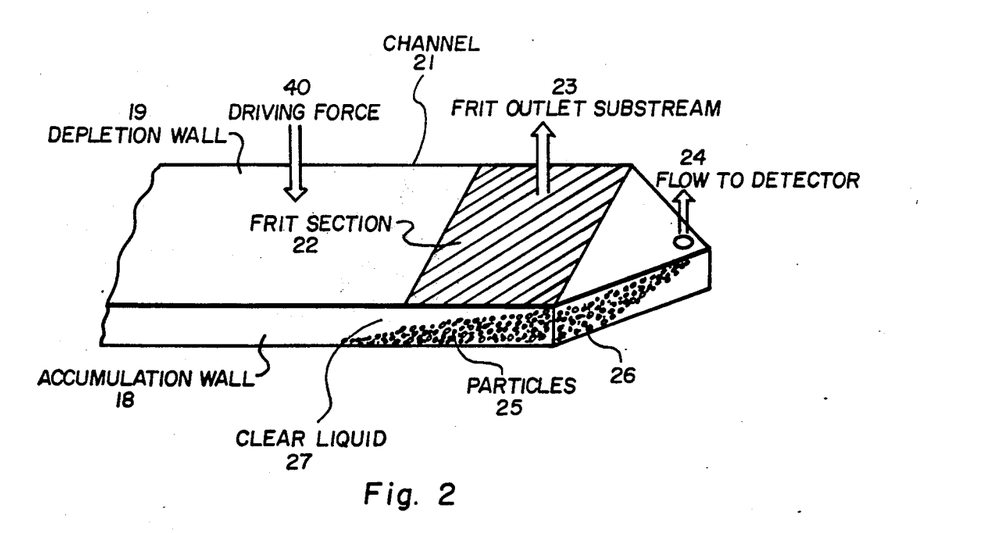
FIG. 2 is a diagram showing the use of an outlet frit section to withdraw (sample free) liquid from above the sample components lying close to the accumulation wail. Removal of the clear liquid leads to sample concentration.

With reference to FIG. 2 which illustrates the presence of frit section 22 at the outlet end of the channel 21, the flow through the frit section constituting the frit outlet substreams is shown as 23, the flow through the normal outlet means as 24, the sample particles being forced through the outlet means as 25. The accumulation wall is shown as 18 and the depletion wall as 19 and the driving force as 40.

Figure 3A:
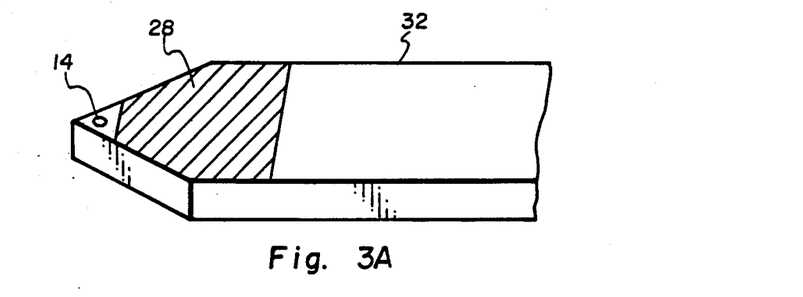
FIGS. 3A, 3B, 3C and 3D illustrate various configurations possible for the inlet frit elements.
Figure 3B:
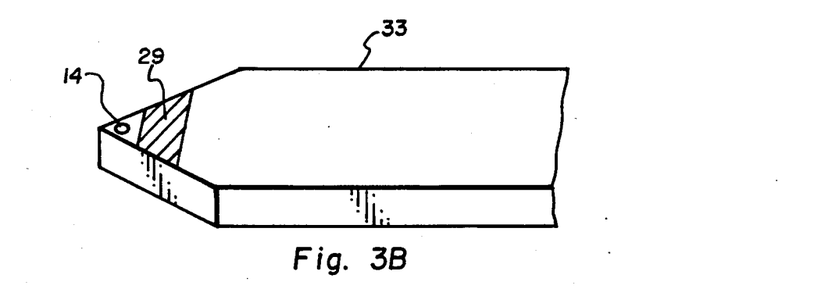
Figure 3C:
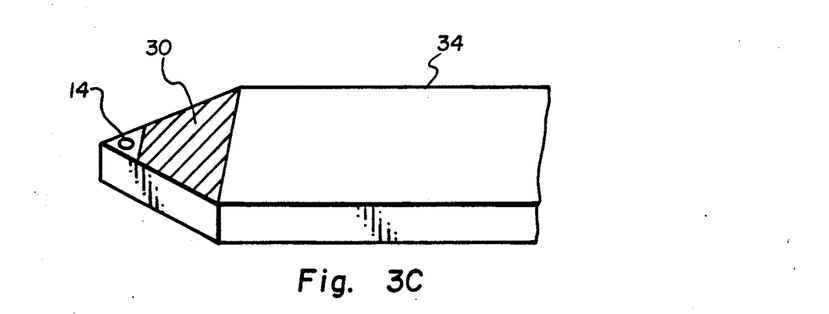
Figure 3D:
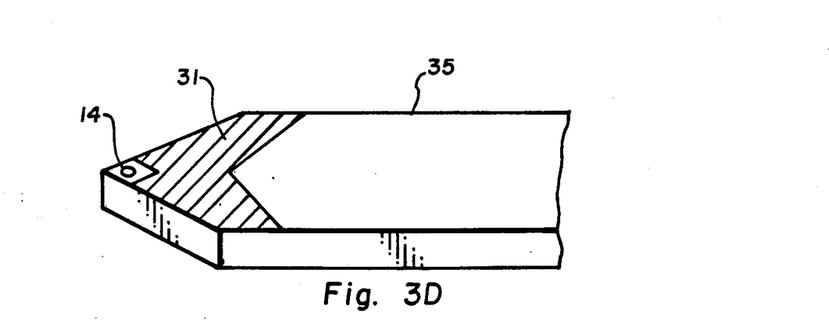

With reference to FIGS. 3A, 3B, 3C and 3D, which show various locations of a frit section at the inlet end, FIG. 3A shows the channel 32, the inlet means for the sample inlet substream as 14 and the location of the frit section as 28. FIG. 3B shows the channel 33, inlet means for the sample inlet substream as 14 and the different location of the frit section as 29. FIG. 3C shows the channel 34, the inlet means for the sample inlet substream as 14 and the new location of the frit section as 30. FIG. 3D shows a channel 35, with the inlet means as 14 and the new configuration of the frit section as 31.

Figure 4:
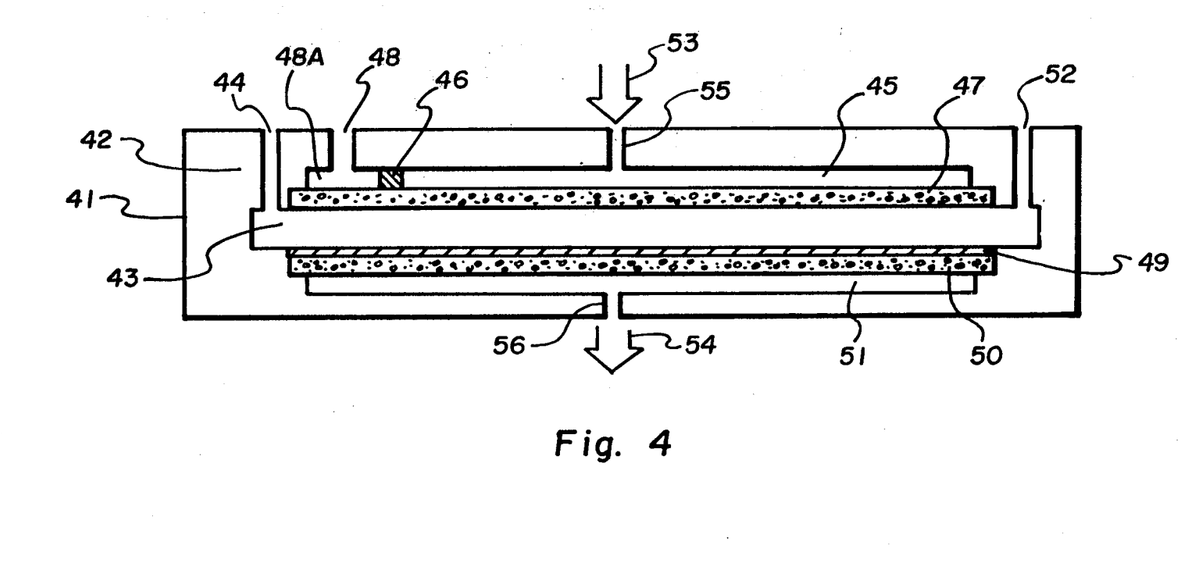
FIG. 4 is a side view illustration of a channel assembly wherein the driving force is cross flow and a dam is used to separate the hydrodynamic relaxation frit section from tho crossflow section.

With reference to FIG. 4 which is a side view of an apparatus 41 illustrating the assembly of apparatus wherein crossflow 53 is the driving force. The Lucite block portion of the apparatus is shown as 42, the channel section as 43, the inlet for the sample substream is shown as 44. The frit constituting the depletion wall is shown as 47, the frit constituting the accumulation wall as 50, a semi-permeable membrane over the frit element 50 is shown as 49. The reservoir for the crossflow is shown as 45, the reservoir for the frit inlet substream 48 is shown as 48A with the dam between the two reservoirs as 46. The reservoir for the crossflow leaving the chamber 54 is shown as 51. The crossflow enters reservoir 45 and leaves chamber 51 by means of holes 55 and 56, respectively. The outlet substream is shown as 52. Crossflow leaving is 54.

FIGS. 5A, 5B, 6A to 6D and FIG. 7 are graphs illustrating results obtained in the experiments disclosed in the Examples at the end of the specification.

DETAILED DESCRIPTION OF THE INVENTION

For clarity, the following definitions will be used throughout the specification and claims.

particle: any sample species that can be retained and separated by FFF methods, including both rigid and deformable particles ranging in size from submicron to hundreds of microns, polymer molecules, biological macromolecules and particles including cells, DNA, and proteins, and any other molecules subject to FFF analysis.

field: any influence that when applied to the FFF channel has the effect of displacing sample particles in a direction perpendicular to the flow axis and thus causing FFF separation.

driving force: the force or effective force acting to displace the particles as a consequence of applying the field.

accumulation wall: the wall toward which sample particles are normally driven by the field.

depletion wall: the wall opposite the accumulation wall, which has particles driven away from it by application of the field.

frit element or section: identical in meaning to permeable wall section.

frit inlet substream: a substream of fluid entering the channel through a frit section near the inlet end.

frit outlet substream: a substream of fluid exiting the channel through a frit section near the outlet end.

sample inlet substream: the substream of fluid that brings the dissolved or suspended sample into the channel. This substream usually enters near the inlet tip of the channel.

sample outlet substream: the substream of fluid carrying sample material out of the channel, normally to a detector. This substream will in most cases exit from the outlet tip of the channel.

As noted, the present invention entails utilizing one or more special sections of permeable wall material (referred to as "frit" elements or sections or permeable wall sections)at one or both ends of the FFF channel through which flow can be freely and independently introduced into the channel or withdrawn from the channel depending upon need. The frit element will normally be embedded smoothly in one or more of the channel walls, thus replacing a small area of the usual wall material. However, in some cases it may protrude further into the channl or it may be recessed, relative to other wall elements. The flow substream(s) entering or departing through the special section(s) are generally complimented by independently controlled flow streams, such as the sample substreams which carry the sample material in or out of the FFF channel. The frit inlet substream is introduced into the channel through the inlet frit section in such a way as to compress the sample inlet substream against one wall which is generally the accumulation wall. The frit outlet substream and the associated outlet frit section are similarly positioned to strip carrier liquid away from the sample at the outlet, leaving the sample material concentrated in the sample outlet substream. To function in these roles, such frit sections will normally constitute part of the depletion wall of the channel, which is the wall opposite the accumulation wall where the sample is concentrated. Their use makes it possible to achieve both hydrodynamic relaxation and sample enrichment without any of the disadvantages noted above for the flow splitters.

In order to distribute the frit inlet substream uniformally over the frit element, a small chamber can be constructed on the backside of the frit section. This chamber serves to collect fluid from the frit inlet substream and distribute it evenly over the area of the frit section.

Hydrodynamic relaxation achieved by the use of the permeable wall section at the inlet is illustrated in FIG. 1. The sample pulse is introduced into a stream of carrier (the sample inlet substream) that enters the inlet end of the FFF channel. A second substream, usually of larger flowrate than the first, is introduced through the permeable wall section, a segment of the depletion wall generally extending across the full breadth of the channel, but only a small fraction of its length. This flow stream (the frit inlet substream) percolates into the channel across the permeable wall section, thereby displacing the sample inlet substream downward toward the accumulation wall. This compression is indicated in FIG. 1 by the downward displacement of the inlet splitting plane, the stream plane that divides the fluid elements entering in the two substreams. The sample material remains below the splitting plane and is thereby compressed to the vicinity of the accumulation wall by the unique configuration of merging flows. This sample compression process is referred to as hydrodynamic relaxation.

As shown in FIG. 1, the permeable wall section used for hydrodynamic relaxation is located close to the inlet. It may extend over all or part of the triangular end piece normally utilized as part of the FFF channel structure. In other cases, it can be positioned partially or entirely beyond the triangular end piece. Several possible configurations of the frit element used at the inlet end are shown in FIGS. 3A, 3B, 3C and 3D. Special shapes can be used to reduce end or edge effects, or otherwise control the details of channel flow.

The achievement of hydrodynamic relaxation by a permeable wall element is expected to be applicable to virtually all forms of FFF including sedimentation FFF, thermal FFF, electrical FFF, and flow FFF in both steric and normal modes of operation. It is expected to be particularly convenient for flow FFF, for which the depletion wall is generally permeable to begin with. A liquid feed chamber usually extends along the length of the permeable wall on its reverse side to distribute incoming carrier fluid uniformly over the area of the wall. All that is needed is to isolate by a sealing arrangement a small feed chamber separate from the main chamber above the area selected to be the permeable wall (frit) section. The frit inlet substream is then fed into this isolated chamber and through the adjacent permeable wall section; the seal prevents this substream from intermixing with the normal crossflow stream entering through the permeable wall section further along the length of the channel. Thus, while the permeable wall may be continuous along the length of the channel, it is effectively divided into two (or more) sections that can be made functionally different by the independent control of flowrates through them. Generally, the permeation rate per unit area of permeable wall will be much higher for the permeable section than for the normal depletion wall downstream, necessitating the proposed isolation of the two.

In asymmetric flow FFF, which normally operates with an impermeable wall the frit section(s) can be placed in the depletion wall in much the same manner as in most other forms of FFF.

A permeable wall section similar to that described above for the inlet can be used at the outlet to enrich the sample. This use is illustrated in FIG. 2. Here one uses the permeable wall section to skim off the "clear" (sample free) carrier liquid flowing above the atmosphere of sample particles or molecules. If not removed by some such means, this carrier mixes with the sample at the outlet and leads to considerable sample dilution. As before, the gentle flow conditions provided by a permeable wall element can systematically withdraw all the fluid above an outlet splitting plane whose initial position is determined by the ratio of the volumetric flowrates of the two outlet substreams.

While it is generally preferred to make the frit section part of the depletion wall, it can also be introduced with success in the accumulation wall, or in both walls at the same time. In addition, the frit element can be placed at the inlet end or the outlet end or at both ends at the same time.

The frit section can be prepared from any permeable material but is preferably a ceramic or metal material having a pore size varying from about 1 $\mu$m to 20 $\mu$m. The frit section is preferably permeable to fluids and liquid, such as, for example, aqueous solutions and organic liquids, although they may be permeable to many other substances, such as gases and the like.

As noted, the frit sections should make up not more than 25% of the total area of the enclosing wall. Preferably the frit sections should make up no more than 10% of the area of any individual wall. In the case of the flow FFF system, the frit sections should make up preferably not more than 5 to 10% of the depletion wall, while the crossflow wall may occupy from 90% to 95% of the wall area.

It should be further noted that it is highly preferred to have the flowrate of fluid entering (or exiting) the frit section larger than the flowrate of the sample inlet (or outlet) substream, preferably at least five times as great. The flowrates for both are independently controlled by conventional pumping and flow control systems.

The conditions to be employed in the FFF systems are well known and fully illustrated in the prior art. For example, the type of particles, macromolecules and polymer molecules (all referred to herein as "particles") to be separated, the carrier fluids, the concentration of particles, the type of field or gradients to be used, strength of field, temperature to separation, rate of flow, recovery techniques and general construction of the FFF channels are all illustrated in the prior cited patents, such as Giddings—U.S. Pat. No. 4,737,268, and so much of that disclosure pertinent to the present invention is incorporated herein by reference.

To illustrate the invention the following example is given. It should be understood, however, that the example is given only for the purpose of illustration and should not be regarded as limiting the invention in any way.

EXAMPLE

An apparatus was assembled as shown schematically in FIG. 4. This apparatus is a conventional flow FFF system modified according to the present invention. The FFF channel in which separation takes place was cut out of a 0.0254 cm thick Mylar spacer. The resulting channel is 38 cm in tip-to-top length and 2.0 cm in breadth, yielding a channel volume of 1.68 mL. Directly beneath the channel is a Diaflo YM10 membrane which serves as the accumulation wall of the channel. Beneath the membrane is a 0.60 cm thick ceramic frit with 6 $\mu$m average pore size. The frit is mounted in a Lucite block directly above a thin chamber (the outlet crossflow chamber) designed to collect the crossflow as it emerges through the frit.

Sandwiched immediately above the channel and serving as the depletion wall is a second slab of ceramic frit mounted in a Lucite block like the first. A thin (0.30 cm) chamber has been cut into the block above the frit identical to the outlet crossflow chamber. This chamber extends to within 0.25 cm of the sample inlet port. This system departs from the convention flow FFF system by the placement of a solid blockage across the breadth of this chamber a short distance from the inlet. In this case, the blockage or dam is located 3.2 cm from the inlet end of the chamber. This dam creates two fluid chambers. The larger chamber extending over most of the frit area becomes an inlet crossflow chamber that receives and distributes the crossflow stream over the bounding frit area. This crossflow stream gives rise to the driving force that controls the FFF separation. The small chamber at the inlet end becomes the frit inlet chamber, a key element of this device that serves to distribute a totally independent flow substream, the frit inlet substream responsible for hydrodynamic relaxation, over the frit area immediately above the small inlet section of the channel where the hydrodynamic relaxation is to be achieved. Because the frit inlet substream is controlled independently of the normal crossflow entering the inlet crossflow chamber, higher pressures can be used and higher flowrates per unit area of frit can be realized. In this way the much higher permeation rates needed to achieve hydrodynamic relaxation can be implemented.

The sample material is introduced into the above system by means of an inlet hole drilled through the lucite and frit immediately to the left of the frit inlet chamber. Bands of sample are introduced into this inlet by means of a 7010 Rheodyne sample injection valve equipped with a 40 $\mu$L sample loop. A piece of Teflon tubing of inner diameter 0.05 cm and length 4.8 cm carries the sample from the valve through the upper block assembly into the tip of the FFF channel.

A metering pump was used to introduce the sample into the channel. Another pump was used to drive the frit inlet substream. The crossflow stream was controlled by a pulse-free syringe pump. Components emerging from the channel were detected by a Beckman Model 153 UV detector operating at 254 nm and connected to a two-pen recorder.

Both outlet flows (crossflow and channel flow) from the system are controlled by pieces of 0.025 cm inner diameter stainless steel tubing acting to restrict flow. The outlet flowrates were measured with a buret and a stopwatch.

The carrier liquid used in this study was distilled water containing 0.1% FL-70 detergent and 0.02% sodium azide. The water was degassed by boiling before use. The system was operated at ambient laboratory temperature 23°±1° C. The sample used consisted of mixtures of polystyrene latex beads. The nominal bead diameters, 5.0, 9.87 and 15.0 $\mu$m are hereinafter referred to as 5, 10 and 15 $\mu$m diameter.

RESULTS

Figure 5A:
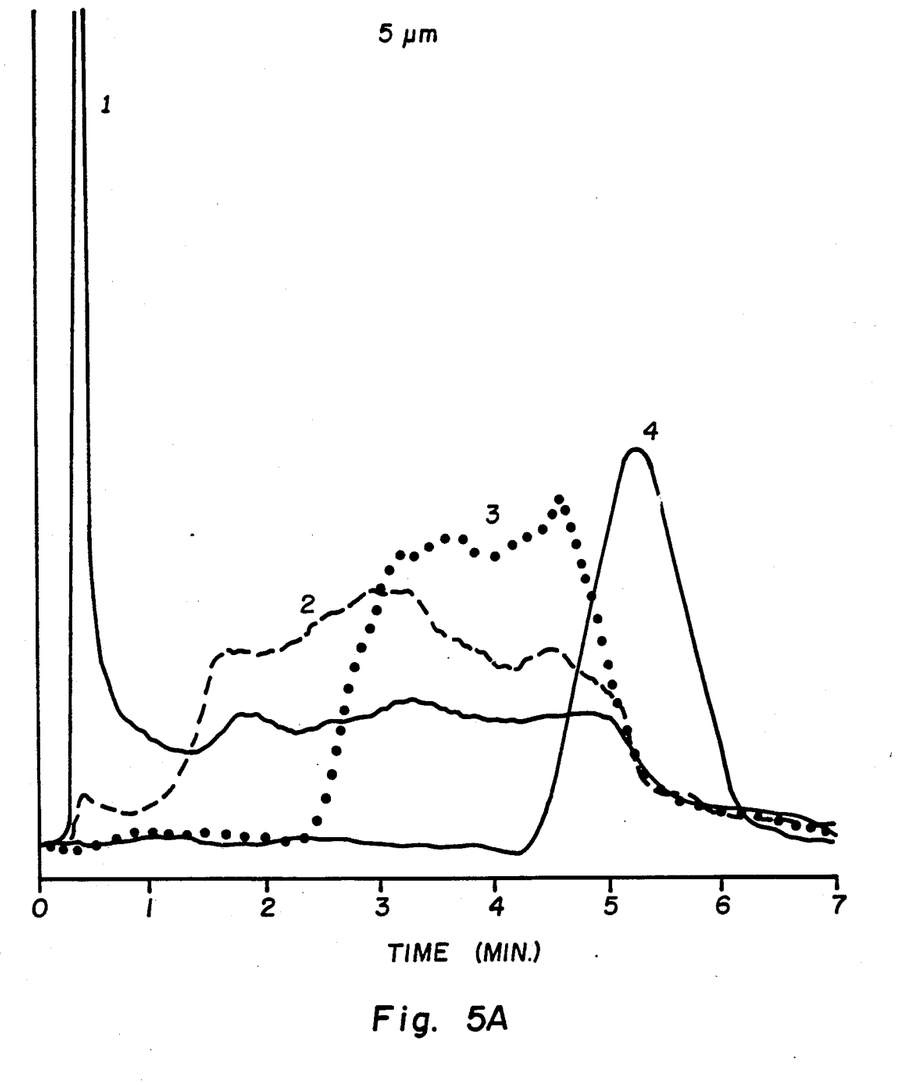
FIG. 5A shows a series of elution profiles for 5 μm latex particles and FIG. 5B shows the elution profiles for 15 μm latex particles observed for stopless flow injection at different levels of hydrodynamic relaxation using a frit inlet section.
Figure 5B:
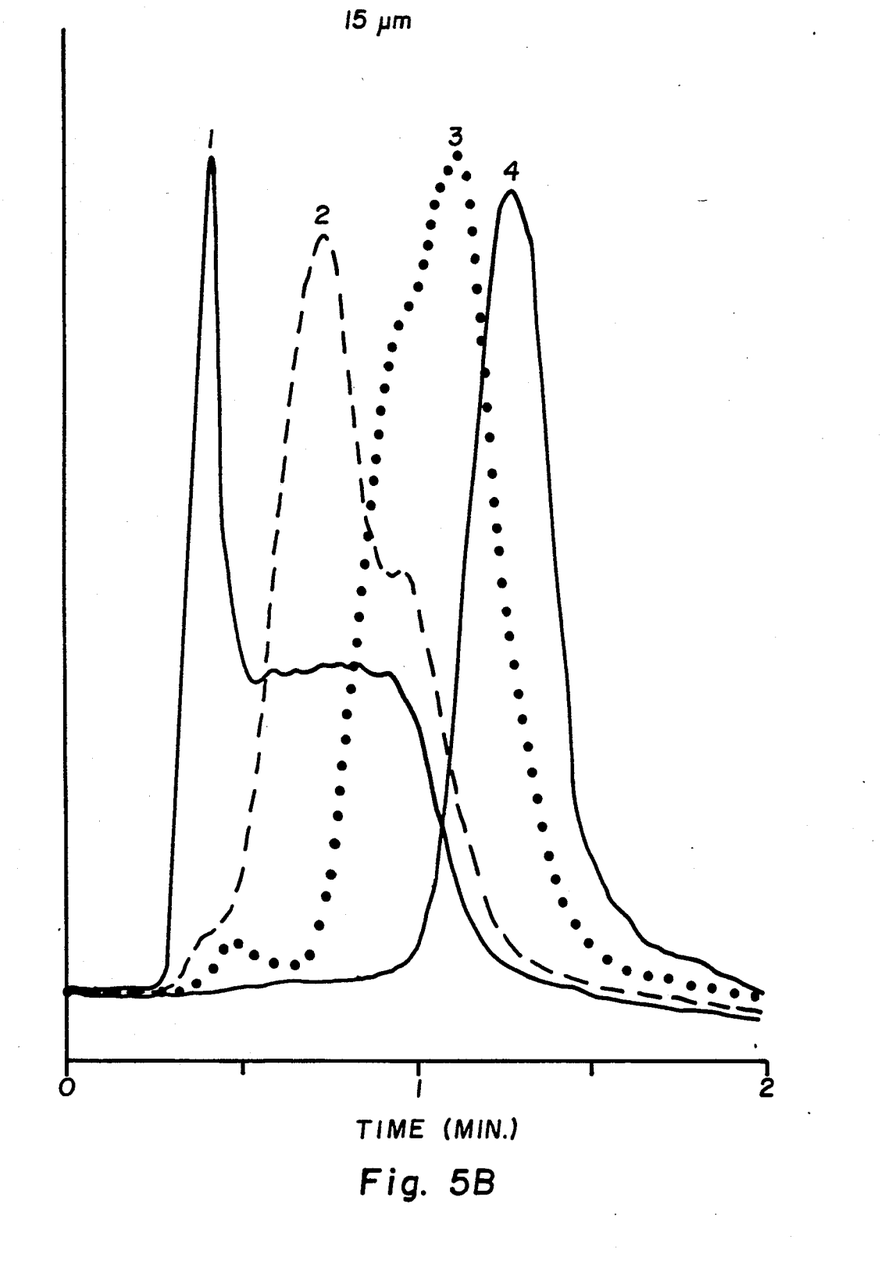
Figure 6A:
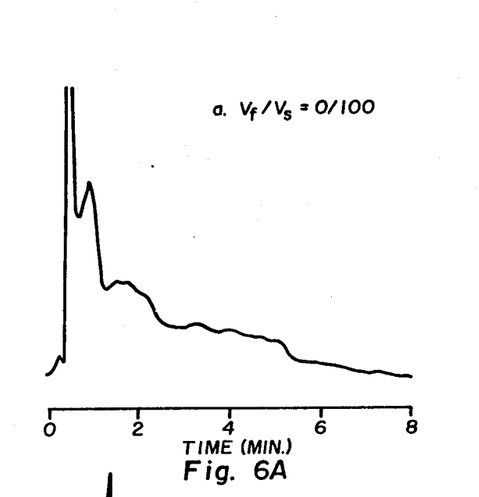
FIGS. 6A, 6B, 6C and 6D illustrate the detector signals as a function of time for the stopless flow injection of 5, 10 and 15 latex beads.
Figure 6B:
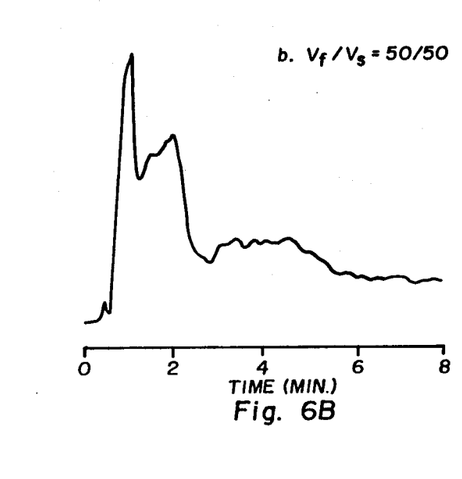
Figure 6C:
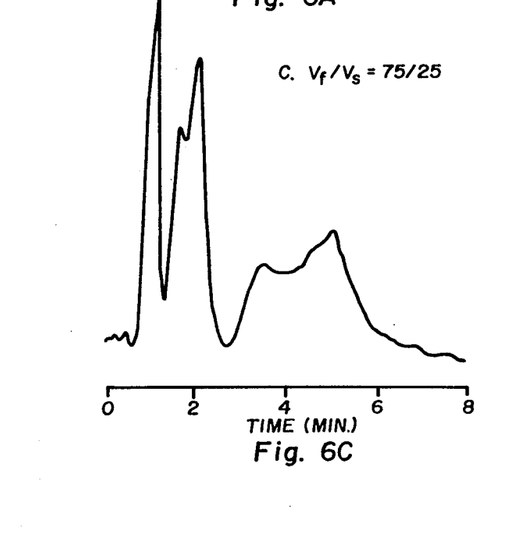
Figure 6D:
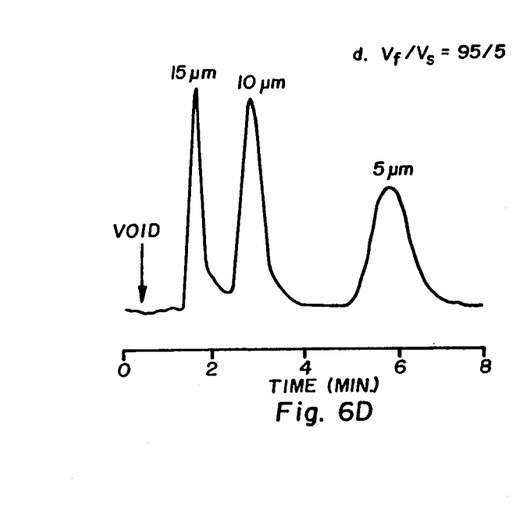

FIGS. 5A and 5B show the elution profiles generated in runs each using particles of a single size, first 5 and then 15 $\mu$m latex beads, at four different flow ratios. The ratio of the frit inlet flowrate $\dot{V}_f$ to the sample inlet flowrate $\dot{V}_s$ increases in the sequence 0/100, 50/50, 75/25, and 95/5 as one proceeds from elution profiles 1 through 4, respectively. In all cases, the total inlet flowrate is $\dot{V}_s+\dot{V}_f=4.1$ mL/min and the crossflow rate is $\dot{V}_c=3.1$ mL/min.

We note that profile 1, for which there is no hydrodynamic relaxation because the frit inlet flow is zero, is very broad in both cases and greatly distorted from the desired Gaussian profile. Such profiles interfere with separation and are not suitable for analytical work. The symmetry and narrowness of the profiles improve from 1 through 4, showing that better results are obtained as one increases the relative level of the frit inlet flow and thus the degree of hydrodynamic relaxation. Similar results were obtained with 10 $\mu$m latex beads.

The effect of the above flow ratio on particle separation is clearly shown in FIGS. 6A, 6B, 6C and 6D. Here the sample consists of a mixture of 5, 10 and 15 $\mu$m latex beads. The overall flow rates are $\dot{V}_s+\dot{V}_f=4.1$ mL/min and $V_c=3.2$ mL/min. The ratio of frit to sample inlet flowrate is again varied through the sequence 0/100, 50/50, 75/25 and 95/5. The resolution of the individual particles, almost nonexistent when the ratio is 0/100 gradually improves with increasing $\dot{V}_f/\dot{V}_s$ until excellent separation is realized when the ratio is 95/5 (FIG. 6). The fractogram at this ratio shows individual, relatively narrow peaks for each of the three particle sizes with each peak well resolved from the neighboring peaks. This figure shows clearly that hydrodynamic relaxation can be realized by employing an inlet frit section and can be used under stopless flow conditions to produce separations that are otherwise not achievable without stopflow.

Figure 7:
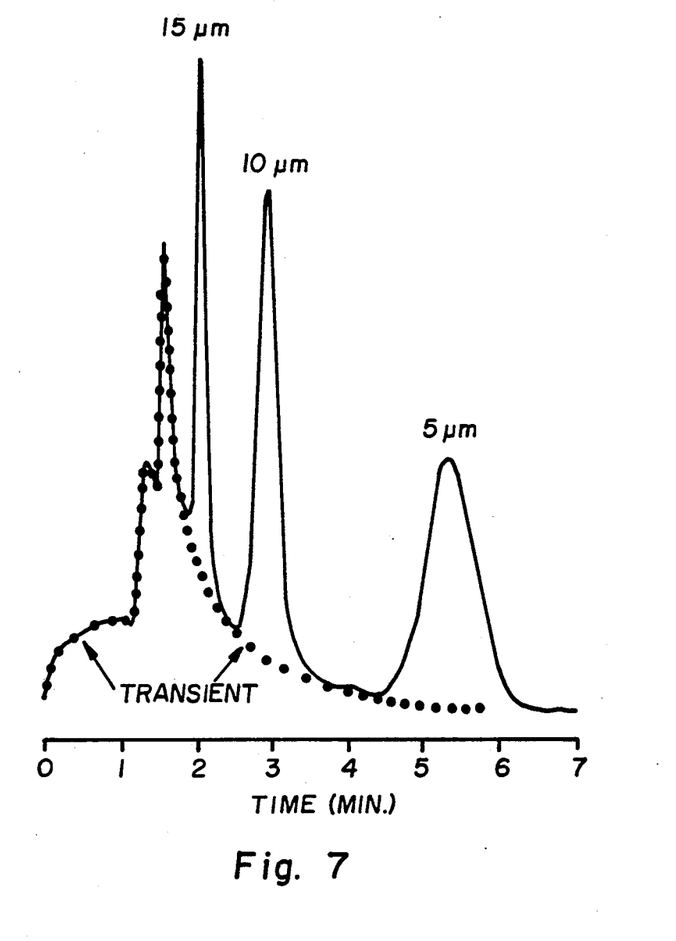
FIG. 7 illustrates the detector signal as a function of time for the separation of 5, 10 and 15 μm latex particles in a frit inlet system using stop flow with inactive frit inlet flow ($V_f=0$).

As noted the stopflow process for sample relaxation not only requires more time and is more conducive to particle adhesion at the wall but it also tends to produce unwanted signal due to pressure pulses caused by abrupt flow changes in the channel. This is illustrated in FIG. 7 in which a 60 second stopflow period is used prior to the run. The channel and crossflow rates for the run are the same as those for FIG. 5. While the stopflow procedure produces peaks that are somewhat sharper than those obtained with hydrodynamic relaxation, the beginning of the run is perturbed by a pressure transient and an unstable baseline that seriously perturbs the measurement of relative particle concentration for all particles above 15 $\mu$m diameter and somewhat perturbs measurements down to diameters below 10 $\mu$m. This unwanted transient is clearly not present where hydrodynamic relaxation has been used as shown in FIG. 5.

The importance of having independent controls of the frit inlet substream and the crossflow streams, as provided by this invention, is illustrated by the above examples. Hydrodynamic relaxation is shown above to be most successful for a 95/5 flow ratio, for which $\dot{V}_f$ is 3.9 mL/min, a value higher than $\dot{V}_c$, 3.1 or 3.2 mL/min. Since the area of the frit section is less than 10% of the area of the depletion wall, the flowrate per unit area is over tenfold greater through the frit section than through the remainder of the depletion wall, requiring a pressure over 10 times higher to drive fluid through the frit section at the amplified rate. The differential flowrates needed for this purpose can only be provided by isolating the frit inlet chamber from the main inlet crossflow chamber and controlling flow to the two chambers independently.

In this specification and accompanying claims the expressions "enclosed wall" or "enclosing wall" are meant to include wall elements enclosing around the thin channel and include straight wall elements as well as curved walls as in a cylinder shaped channel.

I claim as my invention:

1. In a field-flow fractionation process for the separation of particles and polymers wherein a carrier fluid containing the particles to be separated is forced through a thin elongated flow channel having an enclosing wall, an inlet end and an outlet end, and a field or gradient is used to induce a driving force on the particles acting across the thin dimension of the channel perpendicular to the direction of the main channel axis and the particles entering the channel at the inlet end undergo fractionation as they are carried through the channel by flow and emerge as particles fractions at the outlet end, the improvement which comprises feeding at least two independent substreams of carrier fluid into the channel through at least two inlets located at the inlet end, one being the sample inlet, introducing the sample particles into one substream called the sample inlet substream that is forced to enter the channel through the sample inlet, forcing the carrier fluid of the remaining substream or substreams to enter the channel through one or more permeable wall sections whose combined areas constitute less than 25% of the total enclosed wall area of the channel, adjusting the relative flowrates of the different substreams to such proportions that the sample experiences a substantial measure of hydrodynamic relaxation as the substreams merge near the sample inlet.

2. A process as in claim 1 wherein the driving force is generated by a crossflow of fluid in the channel.

3. A process as in claim 1 wherein the driving force is sedimentation.

4. A process as in claim 1 wherein the permeable wall section is made up of a ceramic material having a pore size varying from 1 um to 20 um.

5. A process as in claim 1 in which the substreams enter the channel continuously without interruption for the stopflow procedure.

6. A process as in claim 1 wherein the enclosing wall includes both a depletion wall and an accumulation wall and wherein at least one permeable wall section is incorporated in the depletion wall at the inlet end of the channel.

7. A process as in claim 6 wherein there is an inlet end at the accumulation wall wherein at least one permeable wall section is located at the inlet end of the accumulation wall.

8. A process as in claim 6 wherein the flowrate entering through the permeable wall section or sections is greater than the flowrate entering by means of the sample inlet substream.

9. In a field-flow fractionation process for the separation of particles and polymers wherein a carrier fluid containing the particles to be separated is forced through a thin elongated flow channel having an enclosing wall, an inlet end and a field or gradient is used to induce a driving force on the particles acting across the thin dimension of the channel perpendicular to the direction of the main channel axis, and the particles entering the channel by flow and emerge as particle fractions at the outlet end, the improvement which comprises withdrawing the flowstream consisting of carrier fluid and contained particles flowing along the channel axis through at least two outlets located at the outlet end of the channel, one of the outlet streams called the sample streams detecting the particle fractions emerging in the sample outlet substream, withdrawing the remaining fluid in the flowstream through one or more outlets consisting of one or more permeable wall sections whose combined areas constitute less than 25% of the total wall area of the channel, adjusting the relative flowrates of the different substreams to such proportions that the sample emerging in the sample outlet substrate is more concentrated than it is in the absence of flow through the permeable wall section or sections.

10. A process as in claim 9 wherein the particle fractions emerging from the sample outlet are collected.

11. An improved apparatus for the field flow fractionation comprising an elongated flow channel having an enclosed wall, means for applying a driving force in a direction perpendicular to the direction of the main channel axis, an inlet end and an outlet end, the improvement which comprises at least two separate inlets at the inlet end of the channel, one consisting of the sample inlet through which the sample inlet substream is introduced, and the remainder consisting of at least one permeable wall section, whose combined area constitutes of less than 25% of the total wall area of the channel, through which carrier fluid is introduced for the purpose of hydrodynamic relaxation.

12. An apparatus as in claim 11 wherein the enclosing wall includes both a depletion wall having an inlet end and an accumulation wall.

13. An apparatus as in claim 12 in which there is one permeable wall section located near the inlet end of the depletion wall.

14. An apparatus as in claim 12 in which there is a single permeable wall section located near the inlet end of the depletion wall.

15. An apparatus as in claim 12 wherein at least one permeable wall section is located near the inlet end of the accumulation wall.

16. An apparatus as in claim 12 in which the area of the permeable wall section is less than 10% of the total area of the enclosed wall.

17. An apparatus as in claim 12 wherein the said permeable wall section is made up of ceramic frit material having a pore size between 1 um and 20 um.

18. An apparatus as in claim 12 wherein the driving force is sedimentation.

19. An apparatus as in claim 12 wherein the driving force is generated by a temperature gradient.

20. An apparatus as in claim 12 wherein the driving force is an electrical field.

21. An apparatus as in claim 12 wherein the driving force is generated by a crossflow of fluid in the channel.

22. An apparatus as in claim 12 in which the permeable wall section has a chamber constructed on their backside opposite the channel that serves to distribute fluid over or collect fluid from the permeable wall area.

23. An apparatus as described in claim 12 in which at least one permeable wall element is located near the inlet end and at least one permeable wall element is located near the outlet end.

24. An improved apparatus for field-flow fractionation comprising an elongated flow channel having an enclosing wall, means for applying a driving force in a direction perpendicular to the direction in which the introduced fluid will flow in the channel, an inlet end and an outlet end, the improvement which consists of at least two separate outlets at the outlet end of the channel, consisting of the sample outlet through which the said sample outlet substream is withdrawn, and the remainder consisting of one or more permeable wall section, whose combined area constitute less than 25% of the total wall area of the channel, through which carrier fluid is withdrawn in order to increase the particle concentration in the sample outlet substream.

25. An apparatus as in claim 2 in which the enclosing wall includes both a depletion wall and an accumulation wall.

26. An apparatus as in claim 25 in which at least one permeable wall section is located near the outlet end of the depletion wall.

27. An improved apparatus for field-flow fractionation comprising an elongated flow channel having a permeable depletion wall and a permeable accumulation wall and a driving force wherein the driving force is generated by a crossflow of fluid and on the opposite side of the depletion wall is a flow chamber which extends almost the whole length of the depletion wall, said flow chamber being partitioned into at least 2 separate chambers by impermeable dams, each of the said chambers having its own means for flow ingress or egress.

* * * * *